United States Patent [19]

Yokota et al.

[11] Patent Number: 4,695,542

[45] Date of Patent: Sep. 22, 1987

[54] CDNA CLONES CODING FOR POLYPEPTIDES EXHIBITING MULTI-LINEAGE CELLULAR GROWTH FACTOR ACTIVITY

[75] Inventors: Takashi Yokota; Frank Lee, both of Palo Alto; Donna Rennick, Los Altos Hills; Ken-ichi Arai, Palo Alto, all of Calif.

[73] Assignee: DNAX Research Institute of Molecular and Cellular Biology, Inc., Palo Alto, Calif.

[21] Appl. No.: 590,867

[22] Filed: Mar. 19, 1984

Related U.S. Application Data

[63] Continuation-in-part of Ser. No. 539,050, Oct. 4, 1983, abandoned.

[51] Int. Cl.$^4$ .................. C12P 21/00; C07H 15/12; C12N 15/00; C12N 1/00
[52] U.S. Cl. ........................... 435/68; 435/240; 435/255; 435/172.3; 435/317; 536/27; 935/48; 935/49; 935/50; 935/69; 935/70; 935/71; 435/320; 435/240.26; 435/240.1; 935/13; 935/47
[58] Field of Search .............. 435/68, 240, 255, 172.3, 435/317; 536/27; 935/7, 9, 11, 13, 32, 41, 47, 48, 49, 50, 69, 70, 71

[56] References Cited

U.S. PATENT DOCUMENTS 4,438,032  3/1984  Golde et al. ................ 435/68 X

OTHER PUBLICATIONS

Ihle, J. et al, *J. Immunology*, vol. 131(1), pp. 282–287, Jul., 1983.
Ihle, J. et al, *J. Immunology*, vol. 129(5), pp. 2431–2436, Dec., 1982.
Itakura, K. et al, *Science*, vol. 209, pp. 1401–1405, 1980.
Elder, J. et al, *Ann. Rev. Genet.*, vol. 15, pp. 295–340, 1981.
Moriarty, A. et al, *Proc. Natl. Acad. Sci.*, vol. 78(4), pp. 2606–2610, 1981.
Rennick, D. et al, *J. Immunology*, vol. 134(5), pp. 910–914, 1985.
Yokota, T. et al, *Proc. Natl. Acad. Sci.*, vol. 81, pp. 1070–1074, 1984 (Feb.).
Wong, G. G. et al, *Science*, vol. 228, pp. 810–815, May, 1985.
Fung, M. C. et al, *Nature*, vol. 307, pp. 233–237, Jan., 1984.
Miyatake, et al, *Proc. Natl. Acad. Sci.*, vol. 82, pp. 316–320, 1985.

*Primary Examiner*—Thomas G. Wiseman
*Assistant Examiner*—Jayme Huleatt
*Attorney, Agent, or Firm*—William M. Smith; Stephen C. Macevicz

[57] ABSTRACT

Plasmid vectors are provided that carry complementary DNA (cDNA) clones coding for polypeptides exhibiting mammalian multi-lineage growth cell activity. One of these polypeptides is 166 amino acids in length, including a potential leader sequence of about 19 amino acids. The cDNA is derived from messenger RNA isolated from a mouse T-cell line after activation with concanavalin A. The cDNA was cloned by incorporation into a plasmid vector, which was then transformed into *E. coli*. The plasmid vector also contains DNA segments from the SV40 virus, permitting expression of the cDNA after transfection into a mammalian host cell, such as monkey COS-7 cells.

17 Claims, 4 Drawing Figures

```
                                                                                                                  CTC
GGGGGGGGGG GGGAACCCCT TGGAGGACCA GAACGAGACA ATG GTT CTT GCC AGC ACC AGC ATC CAC ACC ATG CTG CTC
                                                MET Val Leu Ala Ser Thr Ser Ile His Thr MET Leu Leu
 1          20          40         60          80

CTG CTG ATG CTC TTC CAC CTG GGA CTC CAA GCT TCA ATC AGT GGC CGG GAT ACC CGT TTA ACC AGA ACG TTG
Leu Leu MET Leu Phe His Leu Gly Leu Gln Ala Ser Ile Ser Gly Arg Asp Thr Arg Leu Thr Arg Thr Leu
                        100                         120                        140

AAT TGC AGC TCT ATT GTC AAG GAG ATT ATA GGG AAG CTC CCA GAA CCT GAA CTC AAA ACT GAT GAA GGA CCC TCT
Asn Cys Ser Ser Ile Val Lys Glu Ile Ile Gly Lys Leu Pro Glu Pro Glu Leu Lys Thr Asp Glu Gly Pro Ser
                    160                          180                         200                         220

CTG AGG AAT AAG AGC TTT CGG AGA GTA AAC CTG GAA AGC CAA GGA GAA GTG GAT CCT GAG GAC AGA
Leu Arg Asn Lys Ser Phe Arg Arg Val Asn Leu Glu Ser Gln Gly Glu Val Asp Pro Glu Asp Arg
        240                          260                         280                          300

TAC GTT ATC AAG TCC AAT CTT CAG AAA CTT AAC TGT TGC CTG CCT ACA TCT GCG AAT GAC AAC GAT CTG
Tyr Val Ile Lys Ser Asn Leu Gln Lys Leu Asn Cys Cys Leu Pro Thr Ser Ala Asn Asp Asn Asp Leu
                320                         340                          360                       380

TTC ATT CGA GAT CTG GAT GAC TTT CGG AAG AAA CTG AGA TTC TAC ATG GTC CAC CTT AAC GAT CTG GAG ACA GTG CTA
Phe Ile Arg Asp Leu Asp Asp Phe Arg Lys Lys Leu Arg Phe Tyr MET Val His Leu Asn Asp Leu Glu Thr Val Leu
            400                           420                         440                         460

GCC TCT AGA CCA CCT CAG CCC GCA TCT GGC TCC GTC TCT CCT AAC CGT GGA ACC GTG GAA TGT TAA
Ala Ser Arg Pro Pro Gln Pro Ala Ser Gly Ser Val Ser Pro Asn Arg Gly Thr Val Glu Cys
                      480                         500                         520

CDNA CLONES CODING FOR POLYPEPTIDES EXHIBITING MULTI-LINEAGE CELLULAR GROWTH FACTOR ACTIVITY

This application is a continuation-in-part of application Ser. No. 539,050, filed Oct. 4, 1983 abandoned.

FIELD OF THE INVENTION

This invention relates generally to the application of recombinant DNA technology to elucidate the control mechanisms of the mammalian immune response, and more particularly, to the isolation of cDNA clones coding for polypeptides exhibiting multi-lineage cellular and mast cell growth activity.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, to actually control expression of the cDNA and thereby direct synthesis of the encoded product in the host.

This technology has progressed extremely rapidly in recent years, and a variety of exogenous proteins has been expressed in a variety of hosts. By way of example, some of the eukaryotic proteins so-produced include: proinsulin (Naber, S. et al., Gene 21: 95–104 [1983]); interferons (Simon, L. et al., Proc. Nat. Acad. Sci. U.S.A., 80: 2059–2062 [1983] and Derynck, R. et al., Nucl. Acids Res. 1: 1819–1837 [1983]); and growth hormone (Goeddel, D., et al., Nature 281: 544–548 [1979]). (These publications and other referenced materials have been included to provide additional details on the background of the pertinent art and, in particular instances, the practice of invention, and are all incorporated herein by reference.)

For some time, it has been clear that the mammalian immune response was due primarily to a series of complex cellular interactions, coined the "immune network". While it remains clear that much of the response does in-fact revolve around the network-like interactions of lymphocytes, macrophages, granulocytes, and other cells, immunologists now generally hold the opinion that soluble proteins (e.g., the so-called lymphokines) play a critical role in controlling these cellular interactions.

Lymphokines apparently mediate cellular activities in a variety of ways. They have been shown to have the ability to support the proliferation and growth of various lymphocytes and, indeed, are thought to play a crucial role in the basic differentiation of pluripotential hematopoietic stem cells into the vast number of progenitors of the diverse cellular lineages responsible for the immune response. Cell lineages important in this response include two classes of lymphocytes: B cells that can produce and secrete immunoglobulins (proteins with the capability of recognizing and binding to foreign matter to effect its removal), and T cells of various subsets that induce or suppress B cells and some of the other cells (including other T cells) making up the the immune network.

Another important cell lineage is the mast cell—a granule-containing connective tissue cell located proximate to capillaries throughout the body, with especially high concentrations in the lungs, skin, gastrointestinal and genitourinary tracts. Mast cells play a central role in allergy related disorders, particularly anaphylaxis, as follows. Briefly stated, once certain antigens crosslink special immunoglobulins bound to receptors on the mast cell surface, the mast cell degranulates and releases the mediators (e.g., histamine, serotonin, heparin, kinins, etc.) which cause anaphylactic and some other allergic reactions.

Research to better understand (and thus potentially treat therapeutically) allergy, anaphylaxis and other immune disorders, through the study of mast cells, T cells and the other cells involved in the immune response, has been hampered by the general inability to maintain these cells in vitro. However, several immunologists recently discovered that such cells could be isolated and cultured by growing them on secretions from other cells, e.g., conditioned media from Concanavalin A (Con A) stimulated splenic lymphocytes. It has now become clear from this work that the generation of cell clones is dependent on specific factors, such as lymphokines.

All blood cell types are continuously generated in the adult vertabrate bone marrow through the growth and differentiation of the hierarchy of hematopoietic progenitor cells. At the apex of this hierarchy is the pluripotent stem cell which can repopulate a lethally irradiated animal for most, if not all, immunological cell types (e.g., red cells, platelets, lymphocytes, various granulocytes and monocytes/macrophages). The pluripotent cell not only has the capacity to regenerate the pluripotent stem cell compartments (self-renewal), but also gives rise to progenitor cells committed to development along one particular lineage pathway. All the progeny of a particular committed stem cell share the same lineage commitment as the parent cell (Metcalf, D., "Hemopoietic Colonies", Springer Publishing Co., New York, N.Y., [1977]).

In vito studies on hematopoiesis have shown that a number of soluble cloning stimulating factors (CSF) can regulate the growth of these various progenitor cells. Some of these factors have been partially purified and shown to specifically effect stem cells belonging to a particular cell lineage. For example, erthropoietin stimulates more differentiated members of the erythroid hierarchy (Miyake, T., et.al., J. Biol. Chem. 252: 5558, [1977]), whereas another factor (colony stimulating factor-macrophage or CSF-1) preferentially stimulates macrophage growth in semi-solid cultures of bone marrow cells (Stanley, E., and Heard, P., J. Biol. Chem. 252: 4305, [1977]). Another type of growth factor stimulates hematopoietic colonies consisting of single cell types and mixtures of erythrocytes, megakaryocytes, granulocytes, mast cells and monocyte/macrophages (Iscove, N. et.al., J. Cell. Physiol. Suppl., 1: 65–78, [1982]). The range of progenitor cells responsive to this second type of factor indicates that it may be a multi-lineage cellular growth factor (multi-CSF) effecting various committed progenitor cells, and perhaps pluripotential stem cells as well.

Other factors include, for example, interleukin-1 (IL-1), a factor released from macrophages, which induces replication of thymocytes and peripheral T cells (Mizel, S. et al., J. Immunol. 120: 1497–1503 [1978]). Similarly, interleukin-2 (IL-2) and interleukin-3 (IL-3), are both of wherein released by certain stimulated lymphocytes. A very significant characteristic of IL-2 is the ability to support the continuous growth of certain T cells in vitro (Farrar, et al., Ann. N.Y. Acad. Sci. 332: 303–15 [1979]). Likewise, an important characteristic of IL-3 is the ability to support the growth of cell lines having the phenotypic characteristics of mast cells (Ihle, J., et al., Immunological Rev. 63: 5–32 [1982]). A number of other cellular growth properties have been ascribed to IL-3 as well (see, Ihle, J. et. al., J. Immunol. 131: 282–287 and 129: 2431 [1983]).

While both mouse IL-2 and IL-3 have been at least partially characterized biochemically (Gillis, S. et al., J. Immunol. 124: 1954–1962 [1980] and Ihle, J. et al., J. of Immunol. 129: 2431–2436 [1982], respectively), Il-2 is presently the accepted primary factor responsible for T-cell growth, whereas the protein(s) responsible for mast cell growth factor (MCGF) and CSF activity have not been agreed upon to the same extent. It is now though that mouse IL-2 has a molecular weight (probably as a dimer) of approximately 30–35,000 (Simon, P. et al., J. Immunol. 122: 127–132 [1979]—although some variations are recognized (Robb, R. and Smith, K., Molec. Immun. 18: 1087–1094 [1981]); and human IL-2 apparently has a molecular weight of about 15,000 (Gillis, S. et al., Immun. Rev. 63: 167–209 [1982]. Moreover, a cDNA clone coding for human IL-2 has recently been reported (Taniguchi, T., et al., Nature 302: 305–310 [1983]). On the other hand, mouse mast cell growth factors are presently reported as having molecular weights of 45,000 (Nabel, et al., Nature, 291: 332–334 [1981], of 35,000 (Yung, Y., et al., J. Immunol. 127: 794–799 [1981]and of 28,000 (Ihle, J., et al., J. of Immunol. 129: 1377–1383 [1982]). Similar discrepancies surround the CSFs'.

Although the molecular weight differences could be perhaps partially explained by varying amounts of glycosylation, clarification of the issue requires additional structural data, e.g., substantially full length sequence analysis of the molecules in question. Protein sequencing offers, of course, a possible means to solve the problem, but it is very difficult work experimentally and often cannot provide completely accurate, nor full-length, amino acid sequences. Moreover, having the capability of making bulk quantities of a polypeptide exhibiting mammalian MCGF or CSF activity will greatly facilitate the study of the biology of mast cells and other cells involved in the immune response; e.g., by minimizing the necessity of relying on Con A conditioned media for stimulating cell growth. Accurate and complete sequence data on a mouse MCGF and CSF will also serve to simplify the search for human MCGF and CSF proteins. Finally, additional information on any lymphokine will help in evaluating the roles of the various growth factors and cells of the immune network, providing insight into the entire immune system—with the concomitant therapeutic benefits.

Thus, there exists a significant need for extensive nucleotide sequence data on the DNAs coding for, and amino acid sequences of, proteins exhibiting MCGF or CSF activity, as well as a simple and economic method of making substantial quantities of such materials. The present invention fulfills these needs.

SUMMARY OF THE INVENTION

The present invention provides cDNA clones coding for polypeptides exhibiting mammalian multi-lineage cellular growth factor activity. A nucleotide sequence for the cDNAs and a putative amino acid sequence for the associated polypeptide are shown in FIG. 1. The cDNA sequence can be integrated into various vectors, which in turn can direct the synthesis of the corresponding polypeptides in a variety of hosts, including eukaryotic cells, such as mammalian cells in culture.

More specifically, the invention provides a process for producing a polypeptide exhibiting mammalian multi-lineage cellular growth factor activity, the process comprising the steps of:
 (a) providing a vector comprising a nucleotide sequence coding for said polypeptide, wherein the nucleotide sequence is capable of being expressed by a host containing the vector;
 (b) incorporating the vector into the host; and
 (c) maintaining the host containing the vector under conditions suitable for transciption of the nucleotide sequence into said polypeptide.

Preferably, the cDNA sequences are derived from an mRNA sequence coding for the polypeptides, and the host is an organism, such as a eukaryotic cell transfected or transformed with the vector. Further, the vector also preferably comprises a second nucleotide sequence capable of controlling expression of the nucleotide sequence coding for the polypeptide. This second sequence can include a promotor sequence, one or more intron sequences and a polyadenylation sequence, to permit, respectively, transcription, splicing and polyadenylation of the nucleotide sequence coding for the polypeptide.

Particularly, when the host is a mammalian cell, such as a COS-7 monkey cell, the vector contains the promoter sequence of the simian virus 40 (SV40) early region promoter and the polyadenylation sequence of the SV40 late region polyadenylation sequence.

The mouse cDNA sequence of FIG. 1 is capable of hybridizing with other DNA sequences, such as DNA coding for mammalian multi-lineage cellular growth factors from a human cDNA or genomic library. It is noted that the described cDNA sequences seem to contain information for a leader region.

The polypeptides of FIG. 1 are also capable of enhancing mammalian mast cell growth, particularly in vitro. Suitable pharmaceutical compositions can be prepared by adding the polypeptides to therapeutically compatible carriers.

Other features and advantages of the invention will become apparent from the following detailed description, which describes, by way of example, the present invention.

BRIEF DESCRIPTION OF THE FIGURES

FIG. 1 illustrates the nucleotide sequence and putative corresponding amino acid sequence of a cDNA clone exhibiting multi-lineage cellular growth factor activity.

DESCRIPTION OF THE SPECIFIC EMBODIMENTS

In accordance with the present invention, complementary DNA (cDNA) clones are provided for polypeptides exhibiting mammalian multi-lineage cellular growth factor (multi-CSF) activity. After the cDNA sequences have been incorporated in replicable expression vectors, and the vectors transfected into an appropriate host (e.g., a mammalian cell culture), the expressed polypeptide has the ability to allow the expansion of hematopoietic cells to multiple lineages.

An examplary, putative amino acid sequence based on the isolated nucleotide sequence is shown in FIG. 1. A portion of the predicted sequence (amino acids 33 to 41) is identical with the reported NH2-terminal sequence of mouse Interleukin-3 (IL-3) (Ihle, J. et al., J. Immunol. 131, 282-287 [1983]), which had been shown previously to exhibit mouse mast cell growth factor (MCGF) activity (Ihle, J. et al., J. Immunol, 129, 2431-2436 [1982]). The coding region located between the translation start codon (ATG) and the beginning of the sequence contained in IL-3 is rich in hydrophobic amino acids, as would be expected for a leader sequence of a secreted protein. Therefore, the polypeptide's mature form in vivo, as secreted, possibly begins with an Asp residue, as does IL3, and the proceding 20 or so amino acids—constituting the putative leader sequence—are removed by proteolytic processing. Assuming such to be accurate, the mature polypeptide exhibiting MCGF and multi-CSF would consist of 134 amino acids, with a calculated molecular weight of about 15,000. Furthermore, the presence of four potential N-glycosylation sites, i.e., Asn-X-Ser at deduced amino acid positions 42-44, 70-72, 77-79, and 112-114 of the polypeptide (see, Neuberger et al., Glycoproteins 5, 450-490 Elsevier Publishing Co., U.S.A. [1972]) suggest that it would be glycosylated in vivo.

When transfected into COS-7 monkey cells, one of the cDNA clones of this invention directs the synthesis of biologically active MCGF and multi-CSF. Addition of this expressed cloned gene product to cultures of mouse bone marrow cells also allows the expansion of hematopoietic cells committed to multiple lineages; it supports the formation of burst-forming erythroid colonies (BFU-E), granulocyte/macrophage colonies (CFU-G/M), mast cell colones (CFU-mast), as well as colonies of multiple lineages (CFU-Mixed), and sustains multipotential stem cells (CFU-S) in liquid culture. A variety of methods may be utilized to prepare the cDNA's of the present invention. By way of example, total mRNA is extracted (e.g., as reported by Berger, S. et al., Biochemistry 18: 5143-5149 [1979]) from a cell line, which can be a hybrid cell line, producing polypeptides exhibiting mammalin mast cell growth factor activity. The double-stranded cDNAs from this total mRNA are constructed by using primer-initiated reverse transcription (Verma, I., Biochim. Biophys. Acta, 473: 1-38 [1977]) to first make the complement of each mRNA sequence, and then priming for second strand synthesis (Land, H. et al., Nucleic Acids Res., 9: 2251-2266 [1981]). Subsequently, the cDNAs can be cloned by joining them to suitable plasmid or bacteriophage vectors (Rougeon, F. et al., Nucleic Acids Res., 2, 2365-2378 [1975] or Scherer, G. et al., Dev. Biol. 86, 438-447 [1981]) through complementary homopolymeric tails (Efstratiadis, A. et al., Cell, 10, 571-585 [1977]) or cohesive ends created with linker segments containing appropriate restriction sites (Seeburg, P. et al., Nature, 270, 486-494 [1977] or Shine, J. et al., Nature, 270, 494-499 [1977]), and then transforming a suitable host. (See generally, Efstratiadis, A., and Villa-Kormaroff, L., "Cloning of double stranded cDNA", in Setlow, J. and Hollaender, A. (eds.) Genetic engineering, Vol. 1, Plenum Publishing Corp., N.Y., U.S.A. [1982])

A preferred method of obtaining the full-length cloned cDNAs of this invention is the procedure developed by H. Okayama and P. Berg (Mol. and Cell. Biol., 2: 161-170 [1982]). This method has the advantage of placing the cDNA inserts in a bacterial cloning vector and in a position whereby the cDNA can also be directly translated and processed in mammalian cells. Briefly, the first cDNA strand is primed by polydeoxythymidylic acid covalently joined to one end of a linear plasmid vector DNA. The plasmid vector is then cyclized with a linker DNA segment that bridges one end of the plasmid to the 5' end of the cDNA coding sequence. By employing a DNA fragment containing the Simian Virus 40 (SV40) early region promoter and a linker containing a modified SV40 late region intron, the cDNA can be expressed in vitro in COS-7 mouse fibroblasts without further modification. (See generally, Okayama, H. and Berg, P., Mol. and Cell. Biol., 3: 280-289 [1983] and Jolly, D. et al., Proc. Nat. Acad. Sci. U.S.A., 80: 477-481 [1983].)

The desired cDNA clones can also be detected and isolated by hybridization screening with appropriate mRNA samples (Heindell, H. et al., Cell, 15: 43-54 [1978]). Alternatively, the cDNA libraries can be screened by hybrid selection (Harpold, M. et al., Nucleic Acid Res., 5: 2039-2053 [1978] or Parnes, J. et al., Proc. Nat. Acad. Sci. U.S.A., 78: 2253-2257 [1981]) or in Xenopus oocytes (Aurdon, J., Nature, 233: 177-182 [1971]). (See generally, Villa-Komaroff, L. et al., Proc. Nat. Acad. Sci. U.S.A., 75: 3727-3731 [1978]).

Once the cDNA library in the Okayama/Berg plasmid vector has been completed, the cDNA clones are collected, and random pools checked for the presence of the desired cDNAs by hybrid selection, translation, and assay (e.g., by measuring mast cell growth factor activity, the existence of antigenic determinants, or other biological activities). Pools positive by these criteria can then be probed with an appropriate subtracted probe, e.g., cDNA from a B cell line and/or uninduced T cell line. Thereafter, the positive, probed pools are divided into individual clones which are tested by transfection into a suitable host (such as a mammalian cell culture), and the host supernatant assayed for multi-CSF or MCGF activity. Positive clones are then sequenced.

In further describing the procedures relating to preparing cDNA clones of the invention, the mast cell and other lines will be considered first, followed by general descriptions of the procedures of the in vitro translation of mRNA coding for a protein exhibiting MCGF activity; the construction of a cDNA library containing the cDNA sequences; hybrid selection of the library; isolation of full-length cDNA clones in a plasmid vector and subsequent expression in mammalian cells; multi-CSF assays; human multi-CSF and MCGF isolation, subcloning and expression in bacteria and yeast; and purification and formulation. A more detailed description of the entire experimental process will follow thereafter.

Mast Cell and T-Cell Lines

The preferred mast cells for use in connection with the present invention are those developed as described in Galli, J. et al. (J. Cell Biol., 95: 435–444 [1982]). One cloned line, designated MC/9 and deposited at the American Type Culture Collection (accession number ATCC CRL 8306) was grown in Dulbecco's modified Eagles Medium (DME) supplemented with 5% supernatants from a Concanavalin A (Con A) activated T-cell line, designated Cl.Lyl+2−/9 and deposited at the American Type Culture Collection (Accession Number ATCC CRL 8179) (Nabel, G. et al., Nature, 291: 332–334 [1981]). This T-cell line was derived from C57BL/6 mice (Nabel, G. et al., Proc. Natl. Acad. Sci. U.S.A., 78: 1157–1161 [1981]), and was maintained in modified supplemented DME (Nabel et al., Cell, 23: 19–28 [1981]).

The MC/9 cells are used to assay for MCGF activity, preferably by a $^3$H-thymidine incorporation assay according to established methods (e.g., Nabel et al., Nature, 291: 332–334 [1981]). Briefly, MC/9 cells ($10^4$/well) are cultured in flat bottom Falcon microtiter trays in DME supplemented with 4% fetal calf serum, 50 $\mu$M 2-ME, 2 mM glutamine, non-essential amino acids, essential vitamins and varied concentrations of supernatant in a final volume of 0.1 ml. To each culture is added 0.5 Ci $^3$H-thymidine for the last 4 hr of a 24 hr incubation period. The cells are then harvested onto glass filters and the radioactivity measured by liquid scintillation spectrometer.

Multi-CSF activity comprises testing for the ability to act on multipotential progenitor cells, or a number of lineage restricted cells, or both. (See generally, Iscove, N., et.al., J. Cell Physiol. Suppl. 1:65–78, [1982] and Ruppert, S., Exp. Hematol. 11:154–161 [1983].) Basically, the assay conditions allow generation of burst-forming erythroid colonies (BFU-E), granulocyte/macrophage colonies (CFU-G/M) and colonies of mixed lineages (CFU-Mixed) and are performed generally according to the procedures of Metcalf, D., et al., (J. Cell Physiol., 98:401–420 [1979]) and Johnson, G. (J. Cell Physiol., 103:371–383, [1980]).

Isolation and Size Fractionation of mRNA

Total cellular mRNA can be isolated by a variety of methods, e.g., by using the guanidinium-thiocyanate extraction procedure of Chirgwin. et al. (Biochemistry, 18: 5294–5299 [1979]). If this method is utilized, approximately 100 $\mu$g of polyA+ mRNA, selected on columns of oligo (dT) cellulose, is obtained from $1-2 \times 10^8$ activated helper T-cells, such as Cl.Lyl+2−/9. To fractionate the mRNA by size, 100 $\mu$g of polyA+ mRNA is layered on a 10 ml 5–25% sucrose gradient (10 mM Tris.HCl, pH 7.4, 100 mM NaCl, 1 mM EDTA), and centrifuged for 19 hr at 26,000 rpm in a Beckman SW41 rotor. 450 $\mu$l fractions are collected and RNA precipitated with 2 volumes of ethanol. Hybrib Selection and Microinjection of Xenopus Laevis Oocytes Filter hybridizations are preferably performed essentially as described by Parnes et al. (Proc. Natl. Acad. Sci. U.S.A., 78: 2253–2257 [1981]). Aliquots of eluted mRNA are injected into individual Xenopus laevis oocytes by methods well known in the art. Supernatants from viable oocytes are collected after 48 hr, pooled and assayed for activities.

Construction of cDNA Library

The cDNA library can best be constructed using the pcDV1 vector-primer and the pL1 linker fragment (available from P-L Biochemicals Inc., Milwaukee, WI) according to procedures which result in greatly enriched full-length copies of mRNA transcripts, e.g., Okayama, H., and Berg, P. (Mol. Cell Biol., 2, 161–170 [1982] and Mol. Cell Biol., 3, 280–289 [1983]). The plasmic vector, which contains SV40 early promoter and SV40 RNA processing signals, is designed to promote expression of the cloned cDNA segment in mammalian cells.

Using the Okayama and Berg procedure, the cyclized vector-cDNA preparation is transformed into a competent bacterial cell, such as E. coli MC1061 cells (Casadaban, M. and Cohen, S., J. Mol. Biol., 138: 179–207 [1980]) using calcium chloride (Cohen, S. et al., Proc. Nat. Acad. Sci. U.S.A., 69: 2110–2114 [1972]). Starting with 5 $\mu$g of polyA+ RNA from ConA-stimulated Cl.Lyl+2−/9 cells, about $1.5 \times 10^6$ independent transformants are obtained. About $10^4$ clones are picked up individually and inoculated into wells of microtiter plates (Flow Laboratories Inc., McLean, Va.) containing 200 $\mu$l of L-broth, 50 $\mu$g/ml of ampicillin, and 7% DMSO. Sublibraries based on the size of cDNA insert are prepared from total cDNA library as described in Okayama, H. and Berg, P. (Mol. Cell Biol., 3, 280–289 [1983]). Briefly, plasmid DNA is digested with SalI, ClaI, and HindIII separately, and electrophoresed in 1% agarose gel. After staining with ethidium bromide, the gel is sliced into 7 sections corresponding to cDNA insert sized of 0–1, 1 to 2, 2 to 3, 3 to 4, 4 to 5, 5 to 6, and more than 6 kb. DNA is extracted from each slice, recyclized with T4 DNA ligase, and used to transform MC1061. All nucleotide sequencing can be performed according to the procedure of Maxam, A. and Gilbert, W. (Methods Enzymol., 65: 499–560 [1980]).

Preparation of Subtracted cDNA Probe

A $^{32}$P-cDNA probe is enriched for ConA-induced sequence by two cycles of cDNA adsorption in order to remove cDNA sequences common between Cl.Lyl+2−/9 and closely related, but differentiated cells of the immune system, such as B cell myelomas (see, Davis, M. et al., "Isolation of B4 T-Cell Specific Genes", Vitteta, E. and Fox, C. eds., UCLA Symp., pg. 48 [1982]). About 2 $\mu$g of mRNA containing MCGF activity from a sucrose gradient fraction is preferably used as template for reverse transcriptase using oligo (dT) 12–18 primers (available from Collaborative Research, Waltham, Mass.). After hydrolysis of RNA by alkali, $^{32}$P-cDNA is hybridized with 20 $\mu$g of mRNA each from WEHI-231, a B-cell lymphoma (see e.g., Taussig, et al., Immunology 39: 57–60 [1980]), and an NS-1-derived hybridoma (ATCC accession number HB-8113) at 68° C. for 14 hr (cot=5,000). The unhybridized cDNA is separated from cDNA/RNA hybrids by column chromatography on hydroxylapatite. A second subtraction can then be performed with unhybridized $^{32}$P-cDNA using an excess of mRNA (10 $\mu$g) from uninduced Cl.Ly1+2−/9 cells as above (cot=1,100). The single-stranded $^{32}$P-cDNA enriched for ConA induced sequences, constituting approximately 1–2% of the starting material, is then used for colony hybridization (Maniatis, T. et al., "Molecular Cloning, A Laboratory Manual", Cold Spring Harbor Laboratory, U.S.A. [1982]).

DNA Transfections into Monkey Cells

Approximately $1 \times 10^6$ COS-7 monkey fibroblast cells are seeded onto 60 mm plates the day prior to transfection. Transfections are best performed with 15 $\mu$g of plasmid DNA in 1.5 ml of DME containing 50 mM Tris.HCl, pH 7.4, and 400 $\mu$g/ml DEAE-Dextran (Pharmacia Fine Chemicals, Uppsala, Sweden). This solution is then removed after 4 hr and replaced with 2.0 ml DME+4% fetal calf serum. The medium is collected after 72 hr and assayed for MCGF activity as described above.

Multi-CSF Assays

CFU-c Assay (Colony Forming Unit-culture)

Bone marrow cells were harvested from the femurs of C57B1/6 mice. The cells were washed once and a single cell suspension was prepared in Iscove's modified Dulbecco's Medium, [IMDM] (GIBCO, Grand Island, N.Y.)+3% Fetal Calf Serum [FCS] (GIBCO). The single cell suspension was plated in plastic tissue culture dishes and incubated 1-2 hours in a 37° C. incubator with a 6% $CO_2$ to allow cells to adhere to the dish. The non-adherent cells were then removed and in some cases were placed over a discontinuous Percoll (Sigma Chemical Co., St. Louis, MO) gradient consisting of 2 ml layers of 40%, 50%, 60%, 70% Percoll solution (as reported in Kakiuchi, et.al., J. Immunol., 131:109 [1983]). The cells at the various interfaces were harvested separately and washed twice with IMDM+3% FCS. (Alternatively, cells not placed over Percoll were washed once with IMDM+3% FCS). The separate cell pellets were then resuspended at a concentration of 4.5–6 $\times 10^6$ cells/ml in IMDM+15% FCS.

CFU-c's were assayed by using a modification of the methyl-cellulose procedure of Iscove, et.al., (J. Cell Physiol., 83:309 [1974]). FCS (final concentration 25%), 2-mercaptoethanol ($5 \times 10^{-5}$M) penicillin-streptomycin (1:100 of GIBCO stocks), methyl-cellulose (1.1%, 4000 centipoise) cells ($1.5-2 \times 10^5$/ml) and various experimental factors to be tested for CFU-c ability (30%) were mixed and dispensed 1 ml per small petri dish. The plates were incubated 7 days in a 37° C./6% $CO_2$ incubator. They were then scored for colonies using a dissecting microscope (4×). A colony is defined as consisting of 50 or greater cells. Individual colonies were extracted, placed on microscope slides, fixed and stained with Wright/Geims, (See, *Todd-Sanford Clinical Diagnosis By Laboratory Methods*, 15th edition, Davidsohn and Henry (eds.) 137 [1974]). Morphological analysis of cell types present per single colony was then determined.

BFU-E (Burst Forming Unit-Erythroid or CFU-E)

The above procedure was used with the following modifications. Either at the time of plating in methyl cellulose or 3 days later, sheep erythropoeitin (Step III, Connaught Medical Research Laboratories, Philadelphia, Pa.) was added at a concentration of 0.5–1 unit per plate. Eythroid containing colonies (BFU-E or CFU-E) were scored after 10–14 days (from time of plating) as colonies containing visibly read elements. Individual colonies were extracted and stained as above for morphological analysis.

CFU-s (Colony Forming Unit-spleen)

Bone marrow was extracted from femur bones of C57B1/6 mice. Cells were washed twice with Dulbecco's modified Eagle's medium [DME] (GIBCO) and either injected immediately into the tail vein of lethally irradiated (1000 rads) C57B1/6 recipients or treated further. Treatment consisted of the following various procedures: (1) Anti-theta plus complement lysis of the cells, followed either by immediate injection into recipients, or culture for various times under various conditions before injection. (2) Alternatively, no antiserum lysis was performed, and cells were placed immediately into culture under various conditions. The culture conditions were as follows: cells were resuspended at $1 \times 10^6$ cells/ml in medium consisting of DME (GIBCO)+mercaptoethanol ($5 \times 10^{-5}$M), MEM-Vitamins (1:100) (GIBCO), non-essential amino acids (1:100) (GIBCO), L-glutamine (1:100) (GIBCO), penicillin/-streptomycin (1:100) (GIBCO), a mix of arginine, asparagine, and folic acid, 15% FCS (GIBCO), 2 mM sodium pyruvate+various factors to be tested for maintenance of CFU-s (final concentration 25%). This cell preparation was then plated in 24 well tissue culture plates (Falcon) at 1 ml/well and incubated in a 37° C./10% $CO_2$ incubator for various times (minimum of 7 days). Every 3–4 days, non-adherent cells were removed, spun down, resuspended in fresh media containing the appropriate factor, and replated. For assays in which incubation lasted more than 7 days, cells were "moved up" to larger plastic tissue culture vessels in order to maintain all non-adherent cells at a concentration not exceeding $5 \times 10^5$ per ml. At the end of incubtion, cells were washed twice and resuspended in DME (no supplements) and injected into the tail vein of lethally irradiated C57B1/6 mice. Cells were injected either at specific viable cell numbers or specific volume fraction of the culture. Nine to twelve days following injection spleens were excised and placed in Borin's fixative (Mallinkrodt, St. Louis, MO). Spleen colonies were scored as visible nodules on the spleen surface with the aid of a dissecting microscope (4×).

Human Multi-CSF and MCGF cDNA Isolation

DNA clones of rodent genes have been used to identify and isolate DNA encoding the homologous human genes. Because of the relatively low degree of homology between human and rodent genes, the stringency of hybridization conditions must be adjusted to allow for cross-hybridization between sequences which are only 75–80% homologous. Several different experimental protocols have been used to achieve this purpose. For example, the human C$\kappa$ immunoglobulin light chain gene has been isolated using the corresponding mouse C$\kappa$ gene as a probe (Hieter, P. et al., Cell 22: 197–207 [1981]) and mouse transplantation antigen genes have been isolated by hybridization to DNA clones encoding their human counterparts (Steinnetz, T. et al., Cell 24: 125–134 [1981]).

A preferred method entails plating $\gamma$ Phage clones from a library of human genomic DNA (Maniatis, T., et al., Molecular Cloning, A Laboratory Manual, Cold Spring Harbor Laboratory, U.S.A [1982]) at a density of $2 \times 10^4$ to a $5 \times 10^4$ plaques per 150 mM plate on an appropriate host strain, such as *E. coli* LE392. Ten to twenty plates are generally sufficient.

After 10-12 hours incubation at 37° C., the plates are refrigerated for two hours then a 132 mM nitrocellulose filter is applied to the agar surface of each plate. The filter is allowed to remain in contact with the plate for at least five minutes, during which time the filters are keyed to the plates by puncturing with an ink-filled 22-guage needle. The filters are then peeled from the plates and incubated successively for at least two minutes in first 250 ml of 0.1N NaOH, 0.5M NaCl; then in 250 ml of 0.5M Tris.HCl pH 7.5, 1.5M NaCl. The filters are dried on paper towels and then baked at 80° C. for 4-8 hours.

For hybridization, the filters are wetted in 1x SET 0.15M NaCl, 30 mM Tris.HCl pH 8.0, 1 mM Na2 EDTA), then incubated in a solution of 3x SET, 5x Denhardt's (Denhardt, D.T., B.B.R.C. 23: 641-646 [1966]), 10% dextran sulfate, 0.1% SDS, and 50 µg/ml each poly (rA), poly (rC), and poly (rG), at 65° C. for 2 hours (1.5-2 ml/filter) with constant agitation. This solution is then discarded, and the filters are hybridized with 0.5 µg ($\cong 10^8$ cpm) of a nick-translated mouse DNA probe in the same solution (fresh), L1.5-2 ml/filter at 65° C. for 1 hour, then at 55° C. for 12-20 hours. The filters are then washed successively in 3x SET, 1x Denhardts; 0.1% SDS; and 1x SET, 0.1% SDS (10-15 ml/filter) at 55° C. for one hour with gentle agitation. The filters are dried on paper towels, then autoradiographed for 12-24 hours with appropriate film and an intensifying screen. Hybridizing plaques are picked from the agar plates with sterile pasteur pipets, and each is expelled into 1 ml of 0.1M NaCl, 0.01M Tris.HCl pH 7.5, 10 mM MgCl$_2$, 100 µg/ml gelatin, with 50 µl of CHCl$^3$ added. After at least 4-8 hours in the cold, the phage from each plaque are rescreened at low density (2000-4000 plaques/150 mM plate) by a procedure identical to that described above.

In the same manner as described previously in the mouse system, positively hybridizing phage clones verified by re-screening can than be used as a probe to screen random colonies from a human cDNA library. The human cDNA library should be prepared using RNA from an appropriate cellular source, such as human peripheral blood T lymphocytes (see, Gray, P. et al., Nature 295: 503-508 [1972]). Full length cDNA clones can be identified by expression in Cos7 cells, again as was done for the mouse cDNA clones. The isolated human multi-CSF cDNA clones will be able to express a factor capable of stimulating human bone marrow cells.

Expression in *E. coli.* and Yeast and Cell Culture

To express cDNA clones of the present invention in *E. coli.*, suitable promoters (e.g., trp, lac, tac, λpL, etc.) and Shine Dalgarno sequences will be fused with the entire coding sequence of those plasmids carrying an ATG codon in front of the cleavage site of the signal peptide.

pcD-MCGF is first digested with PstI and XhoI endonuclease, and about 1 kb segment containing the entire protein coding sequence is subcloned into the appropriate *E. coli* expression vectors to express the MCGF protein and signal sequence. Alternatively, in order to express only the mature protein, it can be subcloned into the PstI and SalI enconuclease sites of M13mp8. Single stranded M13mp8 DNA containing the complementory strand of MCGF coding sequence is annealed with a synthetic oligonucleotide (5' GAT ACC CAC CGT TTA$^{3'}$), and double stranded protein coding sequence is then synthesized by the Klenow fragment. After digestion with NeoI endonuclease and treatment with S1 nuclease, a blunt ended DNA segment containing the double stranded MCGF a multi-CSF coding sequence is inserted into an appropriate expression vector, such as pDR540—which has the tac promoter (see, Russel, D. R. and Bennett, G. N. Gene 20, 231-243 [1982]; and deBoer, H. et al., Proc. Natl. Acad. Sci. U.S.A. 80, 21-25 [1983]). (See generally, Messing, J. et al., Proc. Nat. Acad. Sci. 74, 3642-3646 [1977]; Gronenborn, B. and Messing, J., Nature 272: 375 [1978]; Messing, J. et al., Nucl. Acid Res. 9, 309 [1981]; and Messing, J. and Vieira, J., Gene 19, 269-276 [1982]).

To express an MCGF or multi-CSF cDNA clone in yeast, the PstI-XhoI fragment carrying a cDNA insert is isolated from pcD-MCGF plasmid, and then cloned into the PstI-SalI sites of pUC8. The resultant plasmid B8/pUC8 is cut with PstI and digested with Bal31 to remove the oligo (dG:dc) block placed upstream of the cDNA. XhoI linker is attached to Bal31-digested DNA, and the plasmids are recovered in *E. coli.* The transformants are analysed to determine the size of the deletion. The XhoI-EcoRI fragment (carrying MCGF or multi-CSF cDNA) is then isolated from one of the deletion derivatives, which should have about a 20 base pair deletion, and cloned into HindIII site of pAAH5 and the EcoRI site of pAAR6 by blunt end ligation using the Klenow fragment. (pUC8, is an M13mp7-derived system useful for insertion mutagenesis and sequencing with synthetic universal primers: See, Vieira, J. and Messing, J., Gene 19: 259-268 [1982]); pcD-X: see Okayama, H. and Berg., P., Mol. Cell. Biol. 3: 280-289 [1983]); pAAH5 and pAAR6 are yeast expression vectors carrying the ADCI promoter and terminator: Ammer, G., "Expression of Genes in Yeast using the ADCI promoter", Methods in Enzymology, 101: 192-201 [1982]).

Various cells in culture can be transfected and/or transformed with the cDNA's of the present invention, and thereafter can produce the associated polypeptides. Suitable cells include 1 for example, HeLa cells, Chinese hamster ovary cells and baby hamster kidney cells in culture.

Purification and Formulations

The multi-CSF and MCGF polypeptides expressed in *E. coli,* yeast or otherwise can be purified according to standard procedures of the art, including ammonium sulfate precipitation, fractionation column chromatography (e.g., ion exhange, gel filtration, electrophoresis, affinity chromatography, etc.) and ultimately, crystallization (see generally, "Enzyme Purification and Related Techniques", Methods in Enzymology, 22: 233-577 [1971]). Once purified, partially or to homogeneity, the polypeptides of the invention may be utilized in pharmaceutical compositions (see below), e.g., for treating parasitic infections of the gastrointestinal tract; or for research purposes, e.g., as a supplement to hematopoietic in mast cell growth media and as an antigenic substance for eliciting specific immunolglobulin useful in immunoassays, immunofluorescent stainings, etc. (see generally, "Immunological Methods", Vols. I & II, Eds. Lefkovits, I. and Pernis, B., Academic Press, New York, N.Y. [1979 & 1981]); and "Handbook of Experimental Immunology", Ed. Weir, D., Blackwell Scientific Publications, St. Louis, MO [1978]).

For preparing pharmaceutical compositions containing the polypeptides described by this invention, such polypeptides are combined in admixture with preferably inert, pharmaceutically acceptable carriers. Suitable carriers and processes for their preparation are well known in the art (see e.g., Remington's Pharmaceutical Sciences and U.S. Pharmacopeia: National Formulary, Mack Publishing Company, Easton, PA [1980]). The preferred course of administration is parenteral and can include mechanical delivery systems, such as transdermal delivery.

Preferably, the pharmaceutical composition is in unit dosage form. In such form, the preparation is subdivided into unit doses containing appropriate quantities of the active component. The quantity of active compound in a unit dose of preparation may be varied or adjusted from 1 μg. to 100 mg., according to the particular application and the potency of the active ingredient. The composition can, if desired, also contain other therapeutic agents.

The dosages may be varied depending upon the requirement of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following experimental information and data are offered by way of example and not by way of limitation.

EXPERIMENTAL

A. Cloned Inducer T cells (1) A clone of T cells Cl.Ly1+2−/9 (ATCC accession number CRL 8306) expressing the Thy 1+Ly 1+2−phenotype is continuously maintained at $0.5 \times 10^{-5}$ cells/ml in Dulbecco's Modified Eagles medium (DME) with 10% heat-inactivated fetal calf serum, $5 \times 10^{-5}$M 2-mercapatoethanol (2-ME), 2 mM glutamine, non-essential amino acids, and essential viatmins conditioned with 25% supernatants from Concanavalin A (Con A)-activated mouse Balb/c spleen cells.

(2) Con A-activation of Cl.Ly1+2−/9 cells. The cells are cultured at $5 \times 10^5$/ml in DME with 4% heat-inactivated fetal calf serum, $5 \times 10^{-5}$M 2-ME, 2 mM glutamine, non-essential amino acids, essential vitamins and 2 μg/ml Con A. After 12-14 hrs. incubation at 37° C. in 10% $CO_2$, the cell suspension is centrifuged at 1500 rpm for 10 minutes. The cell pellets are collected and frozen immediately at −70° C. The supernatants are filtered (Nalgene-0.22 microns) are stored at −20° C. as a source of growth factors. Aliquots of the supernatant are assayed for MCGF activity (see below) to verify the induction of the line by the Con A treatment.

B. Cloned Mast Cells

A mast cell line (MC/9) (ATCC accession number CRL 8179) was cloned by limiting dilution from the liver of a 13-day-old mouse fetus in (DME) with 4% heat-inactivated fetal calf serum (FCS), $5 \times 10^{-5}$M 2-ME and 2 mM glutamine condition by Con A activated Balb/c spleen cells (Nabel et al., Nature 291:332-334 [1981]). The cell clone expresses the Thy 1−, Ly 1−, 2−, Ly 5+ phenotype for surface membrane glycoproteins.

(2) The mast cell clone is continuously maintained with doubling times of 16–18 hours (h) in DME with 10% heat-inactivated fetal calf serum, $5 \times 10^{-5}$M 2-mercaptoethanol and 2 mM glutamine, non-essential amino acids, essential vitamins supplemented with 5% supernatant from Con A-activated inducer T cell clone (see above). The growth of the mast cell clone is dependent on the active growth factor(s) obtained from the supernatant of stimulated Cl.Ly1+2−/9 cells.

C. Biological Assays for MCGF (1) Tritiated Thymidine Incorporation Assay.

(a) $1 \times 10^4$ MC/9 cells were cultured in flat-bottom microtiter trays in 0.1 ml of DME with 4% heat-inactivated fetal calf serum, $5 \times 10^{-5}$M 2-ME, 2 mM glutamine, non-essential amino acids, essential vitamins, and doubling dilutions of test supernatant.

(b) The trays were incubated at 37° C. in 10% $CO_2$. After twenty hours, 0.5 μCi $^3$H-thymidine (New England Nuclear, Boston, Mass.) was added to each culture. Four hours later, the cells were onto filter paper strips, using an automated cell harvester unit. The dried samples were dispensed into liquid scintillation fluid and the cpm were counted in a standard β counter.

(2) Tetrazolium Salt (MTT) Colorimetric Assay.

(a) $1 \times 10^4$ MC/9 cells were cultured in flat-bottom microtiter trays in 0.1 ml of DME Supplemented with co-factors and test supernatant as described in 1.a).

(b) The trays were incubated at 37° C. in 10% $CO_2$. After twenty hours, 0.01 ml of 5 mg/ml MTT (3-(4,5-dimethylthiazol-2-yl)-2,5-diphenyl tetrazolium bromide, Sigma Chemical Co., St. Louis, MO) in phosphate buffered saline (PBS) was added to each culture. Four hours later 0.1 ml of 0.04N HCl in isopropanol was added to each culture and thoroughly mixed. After a few minutes, the plates were read on a Dynatech MR580 Microelisa Auto Reader (Dynatech Instruments, Inc., Torrance, CA), at a wavelength of 570 nm (reference wavelength of 630 nm) and a calibration setting of 1.99.

Isolation of mRNA from Cl.Ly 1+2−/9 cells.

(1) Total cellular RNA was isolated from cells using the quanidine isothiocyanate procedure of Chirgwin, et al., (Biochemistry, 18: 5294–5299 [1979]).

Frozen cell pellets from uninduced or Con A induced Cl.Ly 1+2−/9 were resuspended in guanidine isothiocyanate lysis solution. Twenty ml of lysis solution was used for $1-2 \times 10^8$ cells. Pellets were resuspended by pipetting, then DNA was sheared by 4 passes through a syringe using a 16 guage needle. The lysate was layered on top of 20 ml of 5.7M CsCl, 10 mMEDTA in 40 ml polyallomer centrifuge tube. This solution was centrifuged in a Beckman SW28 rotor (Beckman Instruments, Inc., Palo Alto, CA) for 40 hrs at 15° C. at 25,000 rpm. The guanidine isothiocyanate phase containing DNA was pipetted off from the top, down to the interface. The walls of the tube and interface were washed with 2-3 ml of quanidine isothyanate lysis solution. The tube was cut below the interface with scissors, and the CsCl solution was decanted. RNA pellets were washed twice with cold 70% ethanol. Pellets were then resuspended in 500 μl of 10 mM Tris pH 7.4, 1 mM EDTA, 0.05% SDS. 50 μl of 3M sodium acetate was added and RNA was precipitated with 1 ml ethanol. The RNA was collected by centrifuging and the pellets washed once with cold ethanol.

(2) Poly A+ mRNA isolation. Washed and dried total RNA pellet was resuspended in 900 μl of oligo (dT) elution buffer (10 mM Tris-Cl, pH 7.4, 1 mM EDTA, 0.5% SDS). RNA was heated for 3 min. at 68° C., than chilled on ice. 100 µl of 5M NaCl was added. RNA sample was loaded on 1.0 ml oligo (dT) cellulose column (Type 3, Collaborative Research, Walthem, Mass) equilibrated with binding buffer (10 mM Tris-Cl, pH 7.4, 1 mM EDTA, 0.5M NaCl, 0.5% SDS). Flow-through from the column was passed over the column twice more. The column was then washed with 20 ml binding buffer. Poly A+ mRNA was collected by washing with elution buffer. RNA usually eluted in the first 2 ml of elution buffer. RNA was precipitated with 1/10 volume 3M sodium acetate, pH 6, and two volumes of ethanol. The RNA pellet was collected by centrifugation, washed twice with cold ethanol, and dried. The pellet was then resuspended in water. Aliquots were diluted, and absorbance at 260 nm was determined.

Figure 2:
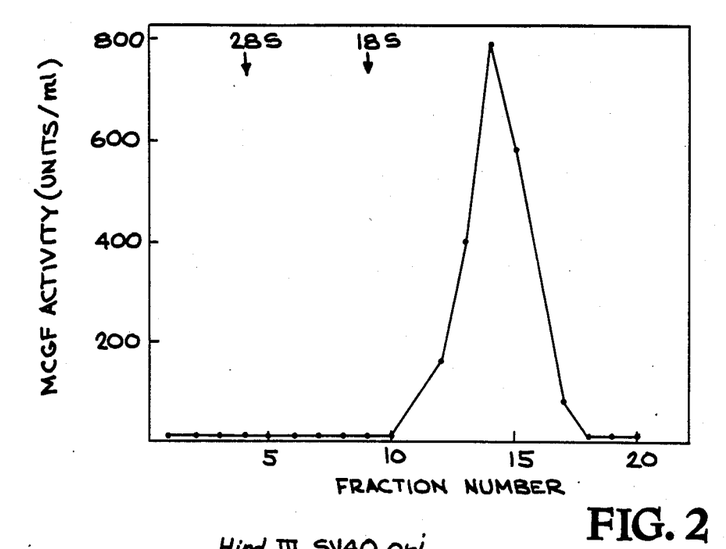
FIG. 2 depicts the amount of MCGF activity in fractions of a sucrose gradient sedimentation of mRNA isolated from ConA stimulated Cl.Ly1+2−/9 cells. The locations of 18S and 28S ribosomal peaks are indicated.

E. Fractionation of poly A+ mRNA by Sucrose Gradient Centrifugation 100 µl containing 100 µg of poly A+ mRNA from above was heated at 65° C. for 1 min. and then layered onto a 10 ml 5–25% sucrose gradient (10 mM Tris.HCl pH 7.4, 100 mM NaCl, and 1 mM EDTA). The gradient was centrifuged in a Beckman SW41 rotor at 26,000 rpm for 19 hours at 5° C. 450 µl fractions were collected, precipitated with 2 volumes of ethanol and resuspended for injection into oocytes (see below). A parallel gradient was layered with a mixture of radiolabelled ($^3$H-Uridine) ribosomal RNA (BRL, Bethesda, MA) centrifuged as described above, and 450 µl fractions were counted in the scintillation counter. The size-fractionated Poly A+ mRNA, following injection in Xenopus oocytes, gave a peak of MCGF activity by the colorimetric assay sedimenting slower than 18S, as shown in FIG. 2. These fractions were enriched approximately 10 fold for MCGF mRNA and were utilized subsequently for the preparation of $^{32}$P-labelled cDNA probe.

F. Oocyte Injection

Oocytes were removed from female *Xenopus laevis* and incubated in Barth's solution (88 mM NaCl, 1 mM KCl, 0.33 mM Ca(NO$_3$)$_2$, 0.41 mM CaCl$_2$, 0.82 mM MgSO$_4$, 2.4 mM NaHCO$_3$, 10 mM HEPES (pH 7.9). Injection clusters of 2–3 oocytes were prepared. RNA samples were to be injected dissolved in injection buffer (40 mM Tris-Cl pH 7.4, 0.35M NaCl). Total poly A+ mRNA was resuspended at a concentration of 500 µg/ml in injection buffer, while RNA samples eluted from DNA filters from hybrid selections (see below) always contained 5 µg of calf liver tRNA as carrier and were resuspended in 2 µl of injection buffer. 40 nl aliquots were injected into each oocyte using micropipets pulled by hand with tips forged using a microforge. The pipettes were calibrated with known volumes of sterile H$_2$O. Approximately 30–40 oocytes were injected for each mRNA sample. The injected oocytes were incubated in groups of two or three in individual wells of 96-well microtiter dishes containing 10 µl of Barth's solution+1% bovine serum albumin per oocyte. The oocytes were kept at 19° C. for 48 hours, then the supernatants from wells containing viable oocytes were collected and pooled. These supernatants were sterilized by centrifuging for 10 minutes in a microcentrofuge, then assayed for MCGF activity as described above. Supernatants from uninjected oocytes were always collected as a control.

The assay results from supernatants collected from untreated on Con A stimulated Cl.Ly1+2−/9 cells are shown in Table I. Titration of all samples and the reference standard were performed in triplicate. One unit of MCGF is the amount of factor that results in 15% of the maximal level of $^3$H-thymidine incorporation obtained using Cl.Ly1+2−/9 supernatant.

TABLE I

| Cl.Ly1+2−/9 Produced MCGF Activity (units/ml) | | |
|---|---|---|
| | Cell Supernatant | Injected mRNA |
| −ConA | 50 | ≦40 |
| +ConA | 26,383 | 1,403 |

G. cDNA Library Construction (1) Preparation of vector primer and oligo dG-tailed linker DNAs. The procedure of Okayama & Berg ([1982] Mol. & Cell. Biol. 2: 161–170) was used with only minor modifications and adapted to the pcDV1 and pL1 plasmids described by Okayama & Berg [Mol. & Cell. Biol. 3: 380–289 (1983)].

An 80 µg sample of pcDV1 DNA was digested at 30° C. with 20 U of KpnI endonculease in a reaction mixture of 450 µl containing 6 mM Tris-hydrochloride (pH 7.5), 6 mM MgCl2, 6 mM NaCl, 6 mM 2-mercaptoethanol, and 0.1 mg of bovine serum albumin (BSA) per ml. After 16 h. the digestion was terminated with 40 µl of 0.25M EDTA (pH 8.0) and 20 µl of 10% sodium dodecyl sulfate (SDS); the DNA was recovered after extraction with water-saturated 1:1 phenol-CHCl$_3$ (hereafter referred to as phenol-CHCl$_3$) and ethanol precipitation. Homopolymer tails averaging 60, but not more than 80, deoxythymidylate (dT) residues per end were added to the KpnI endonuclease-generated termini with calf thymus terminal contained 140 mM deoxynucleotidyl transferase as follows. The reaction mixture (38 µl) sodium cacodylate-30 mM Tris-hydrochloride (pH 6.8) as buffer, with 1 mM CoCl2, 0.1 mM dithiothreitol, 0.25 mM dTTP, the KpnI endonuclease-digested DNA, and 68 U of the terminal deoxynucleotidyl transferase (P-L Biochemicals, Inc., Milwaukee, WI). After 30 min. at 37° C. the reaction was stopped with 20 µl of 0.25M EDTA (pH 8.0) and 10 µl of 10% SDS, and the DNA was recovered after several extractions with phenol-CHCl$_3$ by ethanol precipitation. The DNA was then digested with 15 U of EcoRI endonuclease in 50 µl containing 10 mM Tris-hydrochloride (pH 7.4), 10 mM MgCl$_2$, 1 mM dithiothreitol, and 0.1 mg of BSA per ml for 5 h at 37° C. The large fragment containing the SV40 polyadenylation site and the pBR322 origin of replication and ampicillin resistance gene was purified by agarose (1%) gel electrophoresis was recovered from the gel by a modification of the glass powder method (Vogelstein, B. & Gillespie, D. Proc. Nat. Acad. Aci. 76: 615–619 [1979]). The dT-tailed DNA was further purified by adsorption and elution from an oligo (dA)-cellulose column as follows. The DNA was dissolved in 1 ml of 10 mM Tris-hydrochloride (pH 7.3) buffer containing 1 mM EDTA and 1M NaCl, cooled at 0° C., and applied to an oligo (dA)-cellulose column (0.6 by 2.5 cm) equilibrated with the same buffer at 0° C. The column was washed with the same buffer at 0° C. and eluted with water at room temperature. The eluted DNA was precipitated with ethanol and dissolved in 10 mM Tris-hydrochloride (pH 7.3) with 1 mM EDTA.

The oligo (dG) tailed linker DNA was prepared by digesting 75 µg of pL1 DNA with 20 U of PstI endonuclease in 450 µl containing 6 mM Tris-hydrochloride (pH 7.4), 6 mM MgCl$_2$, 6 mM 2-mercaptoethanol, 50 mM NaCl, and 0.1 mg of BSA per ml. After 16 h at 30° C. the reaction mixture was extracted with phenol-CHCl$_3$ and the DNA was precipitated with alcohol. Tails of 10 to 15 deoxyguanylate (dG) residues were then added per end with 46 U of terminal deoxynucleotidyl transferase in the same reaction mixture (38 μl) described above, except for 0.1 mM dGTP replacing dTTP. After 20 min. at 37° C. the mixture was extracted with phenol-CHCl$_3$, and after the DNA was precipitated with ethanol it was digested with 35 U of HindIII endonuclease in 50 μl containing 20 mM Tris-hydrochloride (pH 7.4), 7 mM MgCl$_2$, 60 mM NaCl, and 0.1 mg of BSA at 37° C. for 4 h. The small oligo (dG)-tailed linker DNA was purified by agarose gel (1.8%) electrophoresis and recovered as described above.

(2) cDNA Library Preparation

Step 1. cDNA synthesis. The reaction mixture (10 μl) contained 50 mM Tris-hydrochloride (pH 8.3), 8 mM MgCl$_2$, 30 mM KCl, 0.3 mM dithiothreitol, 2 mM each dATP, dTTP, dGTP, and dCTP, 20 μCi $^{32}$PdCTP (3000 Ci/mmole), 2 μg polyA+ RNA from Con A induced Cl.Ly1+2−/9, 60 units RNasin (Biotec, Inc., Madison, WI), and 2 μg of the vector-primer DNA (15 pmol of primer end), and 45 U of reverse transcriptase. The reaction was incubated 60 min at 42° C., the stopped by the addition of 1 μl of 0.25M EDTA (pH 8.0) and 0.5 μl of 10% SDS; 40 μl of phenol-CHCl$_3$ was added, and the solution was blended vigorously in a Vortex mixer and then centrifuged. After adding 40 μl of 4M ammonium acetate and 160 μl of ethanol to the aqueous phase, the solution was chilled with dry ice for 15 min., warmed to room temperature with gentle shaking to dissolve unreacted deoxynucleoside triphosphates that had precipitated during chilling, and centrifuged for 10 min. in an Eppendorf microfuge. The pellet was dissolved in 10 μl of 10 mM Tris-hydrochloride (ph 7.3) and 1 mM EDTA, mixed with 10 μl of 4M ammonium acetate, and reprecipitated with 40 μl of ethanol, a procedure which removes more than 99% of unreacted deoxynucleoside triphosphates. The pellet was rinsed with ethanol.

Step 2: Oligodeoxycytidylate [oligo (dC)] addition. The pellet containing the plasmid-cDNA:mRNA was dissolved in 20 μl of 140 mM sodium cacodylate-30 mM Tris-hydrochloride (pH 6.8) buffer containing 1 mM CoCl$_2$, 0.1 mM dithiothreitol, 0.2 μg of poly(A), 70 μM dCTP, 5 μCi $^{32}$P-dCTP, 3000 Ci/mmole, and 60 U of terminal deoxynucleotidyl transferase. The reaction was carried out at 37° C. for 5 min. to permit the addition of 10 to 15 residues of dCMP per end and then terminated with 2 μl of 0.25M EDTA (pH 8.0) and 1 μl of 10% SDS. After extraction with 20 μl of phenol-CHCl$_3$, the aqueous phase was mixed with 20 μl of 4M ammonium acetate, the DNA was precipitated and reprecipitated with 80 μl of ethanol, and the final pellet was rinsed with ethanol.

Step 3: HindIII endonuclease digestion. The pellet was dissolved in 30 μl of buffer containing 20 mM Tris-hydrochloride (pH 7.4), 7 mM MgCl$_2$, 60 mM NaCl, and 0.1 mg of BSA per ml and then digested with 10 U of HindIII endonuclease for 2 h at 37° C. The reaction was terminated with 3 μl of 0.25M EDTA (pH 8.0) and 1.5 μl of 10% SDS, and, after extraction with phenol-CHCl$_3$ followed by the addition of 30 μl of 4M ammonium acetate, the DNA was precipitated with 120 μl of ethanol. The pellet was rinsed with ethanol and then dissolved in 10 μl of 10 mM Tris-hydrochloride (pH 7.3) and 1 mM EDTA, and 3 μl of ethanol was added to prevent freezing during storage at −20° C.

Step 4: Cyclization mediated by the oligo (dG)-tailed tanker DNA. A 9-μl sample of the HindIII endonuclease-digested oligo (dC)-tailed cDNA:mRNA plasmid (90% of the sample) was incubated in a mixture (90 μl) containing 10 mM Tris-hydrochloride (pH 7.5), 1 mM EDTA, 0.1M NaCl, and 1.8 pmol of the oligo (dG)-tailed linker DNA at 65° C. for 5 min, shifted to 42° C. for 60 min, and then cooled to 0° C. The mixture (90 μl) was adjusted to a volume of 900 μl containing 20 mM Tris-hydrochloride (pH 7.5), 4 mM MgCl$_2$, 10 mM (NH$_4$)$_2$SO$_4$, 0.1M KCl, 50 μg of BSA per ml, and 0.1 mM β-NAD; 6 μg of E. coli DNA ligase, and the solution was then incubated overnight at 12° C.

Step 5: Replacement of RNA strand by DNA. To replace the RNA strand of the insert, the ligation mixture was adjusted to contain 40 μM of each of the four deoxynucleoside triphosphates, 0.15 mM β-NAD, 4 μg of additional E. coli DNA ligase, 16 U of E. coli DNA polymerase I, and 9 U of E. coli RNase H. This mixture (960 μl) was incubated successively at 12° C. and room temperature for 1 h each to promote optimal repair synthesis and nick translation by PolI.

Step 6: Transformation of E. coli. Transformation was carried out using minor modifications of the procedure described by Cohen et al., (Proc. Nat. Acad. Sci. USA, 69: 2110–2114 [1972]). E. coli K-12 strain MC1061 (Casadaban, M. and Cohen, S., J. Mol. Biol. 138: 179–207 [1980]) was grown to 0.5 absorbancy unit at 600 nm at 37° C. in 20 ml of L-broth. The cells were collected by centrifugation, suspended in 100 ml of 10 mM Tris-hydrochloride (pH 7.3) containing 50 mM CaCl$_2$, and centrifuged at 0° C. for 5 min. The cells were resuspended in 2 ml of the above buffer and incubated again at 0° C. for 5 min.; then, 0.2 ml of the cell suspensions was mixed with 0.1 ml of the DNA solution (step 5) and incubated at 0° C. for 15 min. After the cells were kept at 37° C. for 2 min. and thereafter at room temperature for 10 min., 0.5 ml of L-broth was added, and the culture was incubated at 37° C. for 30 min., mixed with 2.5 ml of L-broth soft agar at 42° C., and spread over L-broth agar containing 50 μg of ampicillin per ml. After incubation at 37° C. for 12 to 24 h, individual colonies were picked with sterile tooth-picks.

Approximately 1×10$^6$ independent cDNA clones were generated, and of these, 10,000 clones were picked up individually and inoculated into wells of microtiter plates containing 200 μl of L-broth, 50 μg/ml ampicillin, and 7% DMSO Random pools of approximately 1000 clones each were generated, and plasmid DNA prepared for hybrid selection experiments.

H. Hybrid selections

Hybrid selections were performed with eight cDNA plasmid preparations, taken from the random pools described above.

(1) Preparation of DNA filters

All plasmid DNAs were linearized by digestion with ClaI prior to binding to nitrocellulose filters. Digestions were performed in 50 μl containing: 10 mM Tris-Cl pH 7.9, 10 mM MgCl$_2$, 10 μg plasmid DNA, 50 mM NaCl, and 10 units ClaI. Following a 2 hr incubation at 37° C., samples diluted to 200 μl with TE (10 mM tris, pH 8.0, 1 mM EDTA) and extracted with an equal volume (200 μl) of phenol saturated with TE. 20 μl of 3M sodium acetate pH 6 was added to the acqueous phase, and this was precipitated with 2 volumes of ethanol. The DNA pellets were recovered by centrifugation, then washed with 70% ethanol. The dried pellet was resuspended in 150 μl of sterile H₂O for each 10 μl of DNA. Duplicate filters were prepared for each DNA sample, 10 μg DNA per filter. The DNA in 150 μl of H₂O was boiled for 10 min, then 150 μl 1N NaOH was added and the solution incubated 20 min at room temperature. The sample was chilled on ice, then 150 μl 1M HCl, 1M NaCl, 0.3M Na-citrate and 0.5M Tris-CL pH 8.0 was added.

On Oct. 4, 1983, Inventors deposited a culture of *Escherichia coli* stain MC1061 carrying plasmid pcD-MCGF-b9 (also referred to as "pcD-MCGF" and "B-9") with the American Type Culture Collection, Rockville, MD, USA (ATCC) under ATCC accession number 39467. This deposit was made under conditions as provided under ATCC's agreement for Culture Deposit for Patent Purposes, which assures that this deposit will be made available to the U.S. Commissioner of Patents and Trademarks pursuant to 35 U.S.C. 122 and 37 C.F.R. 1.14, and will be made irrevocably available to the public upon issuance of a U.S. patent, which requires this deposit to be permanently maintained. Availability of the deposited strain is not to be construed as a license to practice the invention in contravention of the rights granted under the authority of any government in accordance with its patent laws.

0.9 cm Millipore HAWP filters wet with distilled H₂O were fitted into Schleicher and Schuell micro filtration apparatus. The denatured and neutralized DNA solution was from above was filtered through by centrifugation at 500 rpm for 5 min. Filters were washed with 1 ml of 6XSSC, then air dried before baking 2 hrs. at 80° C.

(2) Hybridizations

Hybridizations were performed in 200 μl containing 65% (v/v) redistilled formamide, 20 mM PIPES, PH 6.4, 0.4M HCCL, 100 μG μg/ml calf liver tRNA, 100 μg/ml polyA+ mRNA from ConA induced Cl.Ly1+2−/9. Each hybridization solution was heated for 3 min at 70° C., then two DNA filters: (10 μg DNA/filter) were cut into quarters and added to the solution. Hybrids were incubated at 50° for 4 hours followed by 4 hour followed by 4 hour incubations at 46° and 42° C. AFter this period the supernatnats were removed and the filters washed 3 times with 1 ml of: 10 mM Tris pH 7.4, 0.15M NaCl, 1 mm EDTA, 0.5% SDS. This was followed by three 1 ml washes with the same buffer lacking SDS. Both buffers were kept at 65° for the washes. To elute the hybridized mRNA, 400 μl of distilled H₂O with 5 μg calf liver tRNA was added to the vial with the filters. The tubes were boiled for 3 min, then quick chilled in dry ice/ethanol. Samples were then thawed, and the eluted RNA precipitated with 2 volumes of ethanol and 1/10 volume 3M Na acetate, pH 6. RNA pellets were collected by centrifugation and washed twice with 70% ethanol. The dried pellets were resuspended in 2μ; of oocyte injection buffer and the entire sample was injected into oocytes (see above).

Of 8 initial pools which were screened in this manner, several were positive, and one pool selecting the highest level of MCGF activity was chosen for further analysis. This pool, which consisted of 672 individual clones was subdivided further into 14 pools of 48 clones each. Plasmid DNA from those pools were used in a second series of hybrid selections. Only one of these sub-pools gave a positive signal. The 48 clones were then screened with the two subtracted cDNA probes as described below.

I. Preparation of Subtracted cDNA probe (1) $^{32}$P-cDNA synthesis:

2 μg of polyA+ mRNA from the MCGF peak fraction of the sucrose gradient from above was resuspended in 2 μl of H₂O. This was heated for 5 min at 65° C., then added to a reaction containing 50 mM Tris-Cl pH 8.3, 8 mM MgCl₂, 30 mM KCl, 0.7 mM DTT, 1 mM each of dATP, dGTP, dTTP, 34 μM dCTP, 10 μg/ml oligo (dt) $^{12\text{-}18}$ (Collaborative Research), 100 μg/ml Actinomycin D, 500 μCi α$^{32}$P-dCTP (Amersham, 3000 Ci/mmole and 150 units reverse transcriptase (Life Sciences, Inc., St. Petersburg, Fla.) in a total volume of 100 μl. Following a 2 hr incubation at 40° C., 0.5 μl of the reaction was removed for precipitation in trichloroacetic acid to determine the amount of $^{32}$P incorporated. Then, 100 μl of 0.2N NaOH was added, and the sample was heated 20 min at 70° C. to hydrolyze the RNA. After cooling, the reaction was reutalized with 20 μl of 1N HCl and 4 μl of 1 mg/ml tRNA was added as carrier. The sample was extracted twice with an equal volume of phenol-chloroform (1:1). It was then precipitated with an equal volume of 4M ammonium acetate and 2 volumes of ethanol. The pellet was resuspended in 100 μl H₂O, the precipitation repeated, and the pellet washed twice with 80% ethanol.

(2) Five subtractive hybridization:

$^{32}$P-cDNA (synthesized as described above) was co-precipitated with 20 μg of polyA+ mRNA from WEHI +3 and 20 μl of poly A+ mRNA from a B-cell hybridoma. The pellet was resuspended in 7 μl H₂O, 1 μl 4M Na Phosphate, pH 7, 0.1 μl 20% SDS, and 0.1 μl 0.1M EDTA, than the entire sample was sealed in a capillary tube. The sample was heated 30 min at 90° C., then shifted to 68° C. for 14 hrs, (Cot=5000). The hybridization mixture was then diluted to 1 ml with 0.12M sodium phosphate pH 7.0, 0.1% SDS, and the temperature of the mixture raised to 60° C. This was loaded on a column of 0.4 gm hydroxylapatite equilibrated in the same buffer and kept at 60° C. The flowthrough was collected and the column was then washed with 5 ml of the same buffer at 60° C. 1 ml fractions were collected and 1 μl aliquots of each fraction were counted in a scintillation counter. The peak of single stranded cDNA in fractions 2, 3, and 4 was pooled. This material representing 66.5% of the starting $^{32}$P-cDNA, was concentrated to 0.4 ml by extraction with 2-butanol, then desalted by chromatography on a 2 ml Sephadex G-25 column.

(3) Second subtractive hybridization:

The desalted sample from above was concentrated by ethanol precipitation, then co-precipitated with 9.5 μg of poly A+ mRNA from uninduced Cl.Ly1+2−/9. The washed, dried pellet was resuspended in 10 μl H₂O, 1.5 μl 4M sodium phosphate, pH 7, 0.15 μl 20 SDS and 0.15 μl M EDTA. The sample was incubated in a sealed capillary tube for 30 min at 90° C., then at 68° C. for 20 hr. Chromatography on hydroxylapatite was repeated as described above. The single stranded cDNA which eluted from the column at 60° C. represented 17% of the starting material. This $^{32}$P-cDNA was used for colony hybridizations of the 48 colonies in the sub-pool identified by hybrid selections. Three colonies hybridized with the probe and were used for further hybrid selection. One of these, designated clone 5G, was reproducibly positive.

J. Size fractionated sub-library

30 μg of plasmid DNA representing the entire cDNA library (pcD-X DNA) was digested separately with the restriction enzymes SalI, HindIII, and ClaI to linearize the plasmid. The restricted DNAs were size fractionated on a 1% agarose gel to separate plasmids having different size cDNA inserts. Segments were excised from the gel representing plasmids with cDNA inserts of the following size ranges:

0–1 kb
1–2 kb
3–4 kb
4–5 kb
5–6 kb
6 kb and longer

DNA was eluted from each gel slice using the glass powder method of Vogelstein and Gillespie Proc. Nat. Acad. Sci. USA, 76: 615–619 [1970]. The eluted DNAs from the 3 digests were pooled on the basis of size, and treated with T4 ligase to recyclize in a total volume of 15 μl containing 50 mM Tris-Cl pH 7.4, 10 mM MgCl$_2$, 10 mM DTT, 1 mM spermidine, 1 mM ATP and 100 μg/ml BSA. The ligation reactions were incubated 16 h at 12° C. 3 μml of each combined size fraction was used to transform E. coli strain MC 1061 using the method of Cohen, et al Proc. Nat. Acad. Sci. U.S.A., 69: 211–2114 [1972]. A library of $1.1 \times 10^5$ independent transformants was obtained for the fraction containing cDNA inserts 1–2 kb in length, which was used for subsequent screening for full length MCGF clones.

K. Screening of Size-fractionated sub-library

Preliminary restriction endonuclease analysis, as well as DNA sequence data, indicated that the cDNA insert for clone 5G (identified by hybrid selection) was approximately 650 base pairs long. An internal BamHl-NcoI restriction fragment was isolated from clone 5G. The fragment was kephosphoryktied with cdf intestinal alkalinse phosphatase according to the method of Chacomas, G. and Sande, J. (Methods Enzymol. 65: 75–79 [1980]. The fragment was then labelled using $\gamma^{32}$P-ATP and T4 polynucleotide kinase according to the method of Maxam, A. and Gilbert, W. (Methods Enzymol. 65: 499–507 [1980]). This labelled fragment was then used to probe an RNA blot of Con A induced Cl.Ly1+2−/9 mRNA. A single band, approximately 1 kb long, was detected, suggesting that clone 5G was not a full-length clone.

We therefore used the same probe from the 5G cDNA insert to screen the sub-library enriched for 1–2 kb inserts (from above). We employed the method of Hanahan and Moselson (Gene, 10: 63 [1980]) as described in Maniatis, T., et al. (Molecular Chem. Cold Spring Harbor Laboratory [1982]). Approximately 500–1000 bacteria were spread on 80 mm nitrocellulose filters, incubated on L-broth plates containing 50 μl/ml ampicillin at 37° C., and the bacterial colonies transferred to a second nitrocellulose filter. The duplicate filters were incubated on L-broth+ampicillin for 8 hrs. at 37° C., transferred to L-broth plates containing 10 μg/ml chloramphenicol and incubated overnight to amplify the copy number of the plasmid. The DNA from the colonies was bound to the nitrocellulose following lysis of the colonies with SDS, denaturation with NaOH and neutralization as described n Maniatis, T. et al., supra.

Approximately 20,000 colonies were screened and 19 colonies were reproducibly positive following rescreening with the probe. Plasmid DNA from these colonies was prepared and used in transfection experiments.

L. DNA Transfections

One day prior to transfection, approximately $10^6$ COS-7 monkey cells were seeded onto individual 60 mm plates in DME containing 10% fetal calf serum and 2 mM glutamine. To perform the transfection, the medium was aspirated from each plate and replaced with 1.5 ml of DME containing 50 mM Tris.HCl, pH 7.4, 400 μg/ml DEAE-Dextran and 15 μg of the plasmid DNAs to be tested. The plates were incubated for four hours at 37° C., then the DNA-containing medium was removed, and the plates were washed twice with 2 ml of serum-free DME. 2.0 ml of DME containing 4% fetal calf serum and 2 mM glutamine was added to the plates which were then incubated 72 hours at 37° C. The growth medium was collected and assayed for MCGF activity as described above.

Five of the six initial positive clones were examined by transfection and the results are shown in Table II. Mock infected COS-7 cells were treated identically, but omitting DNA.

TABLE II

Transient Expression of MCGF in Monkey Cells

| Clone | cDNA Start Point* | Length of Oligo(dG) Block*** | MCGF Activity units/ml |
|---|---|---|---|
| Mock | — | — | ≦20 |
| B4 | 41 | 13 | 5,228 |
| B5 | ND** | ND | 7,371 |
| B6 | 1 | 13 | 3,307 |
| B8 | 1 | 13 | 6,929 |
| B9 | 1 | 13 | 3,362 |
| Cl.Ly1+2−/9 | — | — | 19,769 |

*The 5' end of MCGF cDNA expressed as nucleotide residue in FIG. 1.
**Not determined; cDNA start point is located at the 5' side of position 41.
***Oligo (dG) block at the 5' end of MCGF cDNa.

Figure 3:
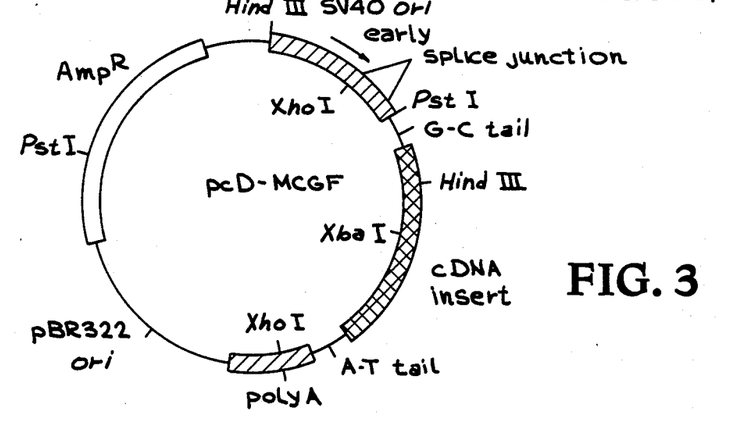
FIG. 3 illustrates pcD-MCGF, a plasmid carrying a cDNA clone exhibiting mast cell growth factor activity and multi-lineage cellular growth factor activity. Transcription of the 950 bp cDNA insert contained in the pcD expression vector from the SV40 early promoter is indicated by the arrow. The location of the splice donor and acceptor sites are shown. The polyadenylation signal, also derived from SV40, is located at the 3' end of the cDNA insert. The cDNA insert is shaded in black. The remainder of the vector sequences are derived from pBR322, including the β-lactamase gene (Amp ®) and the origin of replication.
Figure 4:
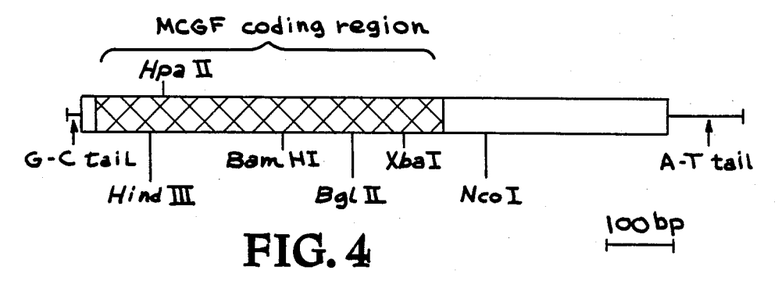
FIG. 4 is a restriction endonuclease cleavage map of the cDNA insert of FIG. 3.

A plasmid (pcD-MCGF) carrying a full-length MCGF and multi-CSF (see below) cDNA insert is shown in FIG. 3, and an E. coli bacteria carrying the plasmid has been deposited with the ATCC (accession number 39467). The 950 bp insert is contained in the pcD expression vector. Transcription from the SV40 early promoter is indicated by the arrow. The location of the splice donor and acceptor sites are shown. The polyadenylation signal, also derived from SV40, is located at the 3' end of the cDNA insert. The cDNA insert is shaded in black. The remainder of the vector sequences are derived from pBR322 including the β-lactamase gene (Amp ®) and the origin of replication. FIG. 4 shows the restriction endonuclease cleavage map of the cDNA insert of the present invention, and FIG. 1 contains the nucleotide sequence and putative amino acid sequence.

Three cDNA inserts contain a single open reading frame consisting of 166 codons beginning with the methionine codon at position 28. In addition to this putative initiation codon, two other methionine codons occur, 12 and 18 codons downstream from the first. A fourth cDNA clone starts 40 base pairs downstream from the 5' ends of the other three inserts. This shorter cDNA clone lacks the first methionine codon but still makes active MCGF upon introduction into COS cells. Thus, one of the two ATG codons downstream can apparently serve as the initiation codon.

MCGF cDNA (clone B9) expressed in COS-7 cells (COS-MCGF) was used to evaluate, in the absence of other T cell products, the spectrum of activities associated with this gene product. COS-MCGF is not mitogenic for T or B cells, fails to induce immunoglobulin production by B cells (Table III), and does not induce macrophage Ia expression. However, this gene product does stimulate the formation of hematopoietic colonies in bone marrow cells suspended in methylcellulose, demonstrating that a single gene product can exhibit both MCGF and colony stimulating activities.

TABLE III

COS-MCGF stimulates BFU-E, CFU-C and CFU-mixed in methylcellulose bone marrow cultures

| Supernatant added to culture | Experiment | Non-erythroid CFU-C* | BFU-E* | CFU-Mixed* | TCGF** Activity Units/ml | BCGF Activity Units/ml | PFC ($10^6$ B cells) |
|---|---|---|---|---|---|---|---|
| COS-7 cells tranfected with MCGF cDNA | 1 | 263 ± 25.5 | 5.3 ± 1.7 | 12.7 ± 1.2 | 0 | 0 | 40 |
|  | 2 | 224 ± 17.6 | 3.3 ± 2 | 4.3 ± 1.1 |  |  |  |
| MOCK transfected COS-7 cells | 1 | 0 | 0 | 0 | 0 | 0 | 33 |
|  | 2 | 1.7 ± 0.6 | 0 | 0 |  |  |  |
| L cells | 1 | 304 ± 25.2 | 0 | 0 | ND | ND | ND |
| Cl.Lyl$^+$2$^-$/9 | 1 | 404 ± 23.0 | 5.0 ± 1.2 | 18.0 ± 2.1 | 3,250 | 512 | 4,560 |
| Medium | 1 | 0 | 0 | 0 | 0 | 0 | 6 |

*Number of colonies per $1.5 \times 10^5$ bone marrow cells. Each value represents mean ± SEM of colonies determined from triplicate cultures. $1.5 \times 10^5$ non-adherent, light density (<1.077 g/ml) bone marrow cells from C57Bl/6 mice were suspended in 1 ml aliquots in 35 mm dishes containing 0.9% methylcellulose, 20% fetal calf serum, Iscove's modified Dulbecco's medium, 50 μM 2-mercaptoethanol, and 30% medium conditioned by cell supernatants as indicated. Mouse L cells were used as a source of CSF, which induces the formation of macrophage colonies. Following 5 days of incubation at 37° C. in $CO_2$, 0.5-1.0 unit of erythropoietin (Connaught Step III) was added to each plate. After incubating the plates for an additional 7 days, the colonies were counted using a dissecting microscope.
**TCGF activity was assayed as previously described. One unit of TCGF activity is defined as that amount which causes 25% of the maximum level of $^3$H—thymidine incorporation in $5 \times 10^3$ HT-2 cells.

B cells were purified from spleen cells of C57Bl/6 mice and assayed for proliferation as described. One unit of BCGF activity is defined as that amount which causes 50% of the level of $^3$H-thymidine incorporation in $1 \times 10^5$ B cells stimulated by 2 μg/ml LPS.

Total immunoglobulin-secreting plaque-forming cells were enumerated by a modification of the hemolytic plaque assay.

Specifically, we tested COS-MCGF under conditions which allow generation of BFU-E, CFU-G/M and CFU-Mixed. Table III shows that three types of colonies could be identified and enumerated in cultures of bone marrow cells incubated with COS-MCGF. The most prevalent type consisted of colorless colonies lacking hemoglobinized elements. Their morphology was typical of granulocyte/macrophage colonies, the existence of which was later confirmed by histochemical standings. Also present were some large macroscopic colonies containing a multicentric arrangement of uniformly red cell clusters, which were designated BFU-E. We further observed a few colonies containing hemoglobinized cells mixed with large and small translucent cells, which were counted as mixed.

The composition of these various colonies was analyzed by applying selected colonies to glass slides and staining with Wright-Giemsa or nonspecific esterase stains. Over 300 colonies were examined. The majority of these colonies (89%) was composed of granulocytes, macrophages or a granulocyte/macropage mixture, while four percent consisted of mast cells. The remainder was composed of mixed lineages other than neutrophil/macrophage. Differential counts of 10 representative mixed colonies compiled from several experiments are presented in Table IV. The presence of several cell types within single colonies suggests that these colonies derive from pluripotent progenitor cells.

TABLE IV

Cellular composition of mixed hematopoietic colonies picked from bone marrow cultures grown in COS-MCGF conditioned medium

| Colony Number | Differential Counts (%) | | | | | | |
|---|---|---|---|---|---|---|---|
|  | E | n | m | e | mast | M | Bl |
| 1 | 21 |  |  |  | 76 |  | 3 |
| 2 |  | 36 | 35 | 20 | 9 |  |  |
| 3 | 97 |  | 1 |  |  |  | 2 |
| 4 |  |  | 22 |  | 78 |  |  |
| 5 | 17 |  | 74 |  | 9 |  |  |
| 6 |  | 64 | 15 | 21 |  |  |  |
| 7 | 18 | 81 |  |  |  | 1 |  |
| 8 | 27 | 40 |  | 33 |  |  |  |
| 9 |  |  | 86 | 14 |  |  |  |
| 10 | 96 |  |  |  | 3 |  | 1 |

*Differential counts of greater than 200 nucleated cells/colony. Abbreviations used are; E, erythrocyte; n, neutrophil; m, macrophage/monocyte; e, eosinophil; mast, mast cell; M, megakayrocyte; and Bl, blast cell.

We also assessed the effects of COS-MCGF on early uncommitted stem cells according to a modified CFU-S assay (Schrader, J., and Clark-Lewis, I., J. of Immunol., 129: 30-35 [1982]) of Till and McCulloch (Radiat. Res., 14: 213-222 [1961]). When non-adherent bone marrow cells, depleted of T cells, were incubated for one week in COS-MCGF medium and injected by vein into lethally irradiated mice, macroscopic colonies appeared in the spleen (Table V). In contrast, cells incubated in supernatants of mock transfected COS-7 cells formed no colonies.

TABLE V

Detection of CFU-S in bone marrow cells cultured for one week in COS-MCGF conditioned medium.

| Supernatant added to culture | Experiment Number | Spleen nodules/ mouse* | CFU-S** |
|---|---|---|---|
| COS-7 cells transfected with full-length MCGF cDNA | 1 | 8.8 ± 1.5 | 264 |
|  | 2 | 6.2 ± 2.8 | 186 |
| COS-7 cells transfected with incomplete MCGF cDNA | 2 | 0.8 ± 0.7 | 24 |
| Mock transfected COS-7 cells | 1 | 0.8 ± 0.7 | 24 |
|  | 2 | 0.7 ± 0.6 | 21 |
| L cells | 1 | 0.3 ± 0.5 | 9 |
|  | 2 | Not done | — |
| Medium | 1 | 0.3 ± 0.5 | 9 |

TABLE V-continued
Detection of CFU-S in bone marrow cells cultured for one week in COS-MCGF conditioned medium.

| Supernatant added to culture | Experiment Number | Spleen nodules/ mouse* | CFU-S** |
|---|---|---|---|
| | 2 | 0.5 ± 0.5 | 15 |

*The mean ± SEM of spleen colonies detected in 5 individual mice.
**The mean of CFU-S calculated to reflect the frequency of CFU-S in the total culture of 3 × 10⁶ bone marrow cells.
Incomplete MCGF cDNA clone lacks the coding region for the NH₂-terminal 55 amino acids
Light density (<1.077) C57B1/6 bone marrow cells treated with anti-Thy1 antibody and complement were plated at 1 × 10⁶ cells/ml in Iscove's modified Dulbecco's medium supplemented with 20% fetal calf serum, 50 μM 2-mercaptoethanol and 30% conditioned medium, as indicated above. Non-adherent cells were removed three times during the one week incubation period and replated in fresh medium. The cells were harvested after one week, washed twice and diluted to the original culture volume in phosphate buffered saline. Each lethally-irradiated (1,000 R) C57B1/6 recipient was injected i.v. with 0.1 ml of the cell suspension. After 9 days, the spleens were removed and the spleen nodules were counted using a dissecting microscope.

To summarize, in addition to the mast cell growth factor activity characterized initially, COS-MCGF has erythroid burst-promoting activity and allows expansion of stem cells and early committed progenitor cells of several lineages, including monocytic/granulocytic, erythroid and megakaryocytic cells. This range of activities indicates that the cDNA clones of the present invention encode proteins having the characteristics of hematopoietic growth factors for cells for multiple lineages.

From the foregoing, it will be appreciated that the cDNA clones of the present invention provide accurate and complete sequence data on mammalian multi-CSF and mast cell growth factors. The invention also provides to those skilled in the art means for producing significant quantities of such factors for the improved in vitro maintenance of mast cells and other hematopoietic cells. Further, the information gleaned from the cDNA clones increases understanding of the mammalian immune response, enhancing therapeutic potentialities.

Although the invention has been described in some detail by way of illustration and example, it will also be apparent that various changes and modifications can be made without departing from the scope and spirit of the appended claims.

We claim:

1. A process for producing a polypeptide exhibiting mouse multi-lineage cellular growth factor activity, said process comprising the steps of:

providing a vector comprising a nucleotide sequence coding for said polypeptide, wherein the nucleotide sequence is capable of being expressed by a host containing the vector and wherein the nucleotide sequence is selected from the group of nucleic acids capable of encoding a polypeptide having an amino acid sequence defined by the formula:

Asp—Thr—His—Arg—Leu—Thr—Arg—Thr—
—Leu—Asn—Cys—Ser—Ser—Ile—Val—Lys—
—Glu—Ile—Ile—Gly—Lys—Leu—Pro—Glu—
—Pro—Glu—Leu—Lys—Thr—Asp—Asp—Glu—
—Gly—Pro—Ser—Leu—Arg—Asn—Lys—Ser—
—Phe—Arg—Arg—Val—Asn—Leu—Ser—Lys—
—Phe—Val—Glu—Ser—Gln—Gly—Glu—Val—
—Asp—Pro—Glu—Asp—Arg—Tyr—Val—Ile—
—Lys—Ser—Asn—Leu—Gln—Lys—Leu—Asn—
—Cys—Cys—Leu—Pro—Thr—Ser—Ala—Asn—
—Asp—Ser—Ala—Leu—Pro—Gly—Val—Phe—
—Ile—Arg—Asp—Leu—Asp—Asp—Phe—Arg—
—Lys—Lys—Leu—Arg—Phe—Tyr—Met—Val—
—His—Leu—Asn—Asp—Leu—Glu—Thr—Val—

-continued
—Leu—Ala—Ser—Arg—Pro—Pro—Gln—Pro—
—Ala—Ser—Gly—Ser—Val—Ser—Pro—Asn—
—Arg—Gly—Thr—Val—Glu—Cys incorporating the vector into the host; and maintaining the host containing the vector under conditions suitable for expression of the nucleotide sequence into said polypeptide.

2. The process of claim 1 wherein said nucleotide sequence coding for said polypeptide further includes a region of nucleotides capable of encoding a leader sequence.

3. The process of claim 1 wherein said vector comprises said nucleotide sequence coding for said polypeptide; said nucleotide sequence being linked to a second nucleotide sequence, wherein the second nucleotide sequence comprises a promoter sequence which promotes expression of said nucleotide sequence in said host.

4. The process of claim 2 wherein said leader sequence is defined by the formula:

Met—Leu—Leu—Leu—Leu—Leu—Met—Leu—Phe—His—
—Leu—Gly—Leu—Gln—Ala—Ser—Ile—Ser—Gly—Arg—.

5. The process of claim 3 wherein said host is a yeast cell.

6. The process of claim 5 wherein said polypeptide is glycosylated.

7. The process of claim 3 wherein said host is a mammalian cell.

8. The process of claim 7 wherein said second nucleotide sequence comprises an SV40 virus early region promoter and further comprises and SV40 virus late region polyadenylation sequence.

9. The process of claim 8 wherein said polypeptide is glycosylated.

10. The process of claim 8 wherein said mammalian cell is selected from the group consisting of COS 7 monkey cells and Chinese hamster ovary cells.

11. A nucleic acid which encodes for a polypeptide exhibiting mouse multi-lineage cell growth factor activity selected from a group consisting of mouse nucleic acids at least seventy-five percent homologous to the nucleotide sequence defined by the formula:

GAT—ACC—CAC—CGT—TTA—ACC—AGA—ACG—
—TTG—AAT—TGC—AGC—TCT—ATT—GTC—AAG—
—GAG—ATT—ATA—GGG—AAG—CTC—CCA—GAA—
—CCT—GAA—CTC—AAA—ACT—GAT—GAT—GAA—
—GGA—CCC—TCT—CTG—AGG—AAT—AAG—AGC—
—TTT—CGG—AGA—GTA—AAC—CTG—TCC—AAA—
—TTC—GTG—GAA—AGC—CAA—GGA—GAA—GTG—
—GAT—CCT—GAG—GAC—AGA—TAC—GTT—ATC—
—AAG—TCC—AAT—CTT—CAG—AAA—CTT—AAC—
—TGT—TGC—CTG—CCT—ACA—TCT—GCG—AAT—
—GAC—TCT—GCG—CTG—CCA—GGG—GTC—TTC—
—ATT—CGA—GAT—CTG—GAT—GAC—TTT—CGG—

—AAG—AAA—CTG—AGA—TTC—TAC—ATG—GTC—

—CAC—CTT—AAC—GAT—CTG—GAC—ACA—GTG—

—CTA—GCC—TCT—AGA—CCA—CCT—CAG—CCC—

—GCA—TCT—GGC—TCC—GTC—TCT—CCT—AAC—

—CGT—GGA—ACC—GTG—GAA—TGT.

12. The nucleic acid of claim 11 defined by the formula:

GAT—ACC—CAC—CGT—TTA—ACC—AGA—ACG—

—TTG—AAT—TGC—AGC—TCT—ATT—GTC—AAG—

—GAG—ATT—ATA—GGG—AAG—CTC—CCA—GAA—

—CCT—GAA—CTC—AAA—ACT—GAT—GAT—GAA—

—GGA—CCC—TCT—CTG—AGG—AAT—AAG—AGC—

—TTT—CGG—AGA—GTA—AAC—CTG—TCC—AAA—

—TTC—GTG—GAA—AGC—CAA—GGA—GAA—GTG—

—GAT—CCT—GAG—GAC—AGA—TAC—GTT—ATC—

—AAG—TCC—AAT—CTT—CAG—AAA—CTT—AAC—

—TGT—TGC—CTG—CCT—ACA—TCT—GCG—AAT—

—GAC—TCT—GCG—CTG—CCA—GGG—GTC—TTC—

—ATT—CGA—GAT—CTG—GAT—GAC—TTT—CGG—

—AAG—AAA—CTG—AGA—TTC—TAC—ATG—GTC—

—CAC—CTT—AAC—GAT—CTG—GAC—ACA—GTG—

—CTA—GCC—TCT—AGA—CCA—CCT—CAG—CCC—

—GCA—TCT—GGC—TCC—GTC—TCT—CCT—AAC—

—CGT—GGA—ACC—GTG—GAA—TGT.

13. A vector comprising a nucleotide sequence capable of expressing a polypeptide comprising the sequence of amino acids defined by the formula:

Asp—Thr—His—Arg—Leu—Thr—Arg—Thr—
—Leu—Asn—Cys—Ser—Ser—Ile—Val—Lys—
—Glu—Ile—Ile—Gly—Lys—Leu—Pro—Glu—
—Pro—Glu—Leu—Lys—Thr—Asp—Asp—Glu—
—Gly—Pro—Ser—Leu—Arg—Asn—Lys—Ser—
—Phe—Arg—Arg—Val—Asn—Leu—Ser—Lys—
—Phe—Val—Glu—Ser—Gln—Gly—Glu—Val—
—Asp—Pro—Glu—Asp—Arg—Tyr—Val—Ile—
—Lys—Ser—Asn—Leu—Gln—Lys—Leu—Asn—
—Cys—Cys—Leu—Pro—Thr—Ser—Ala—Asn—
—Asp—Ser—Ala—Leu—Pro—Gly—Val—Phe—
—Ile—Arg—Asp—Leu—Asp—Asp—Phe—Arg—
—Lys—Lys—Leu—Arg—Phe—Tyr—Met—Val—
—His—Leu—Asn—Asp—Leu—Glu—Thr—Val—
—Leu—Ala—Ser—Arg—Pro—Pro—Gln—Pro—
—Ala—Ser—Gly—Ser—Val—Ser—Pro—Asn—
—Arg—Gly—Thr—Val—Glu—Cys whenever said vector is incorporated into a host.

14. The vector of claim 13 wherein said host is a mammalian cell.

15. The vector of claim 14 consisting of pcD-MCGF-b9 deposited with the American Type Culture Collection under accession number 39467.

16. A microorganism of cell transformed or transfected with the vector of claim 13.

17. The microorganism or cell of claim 16 selected from the group consisting of COS 7 monkey cells and Chinese hamster ovary cells.

* * * * *